(12) United States Patent
Yano et al.

(10) Patent No.: US 7,714,288 B2
(45) Date of Patent: May 11, 2010

(54) CHARGED PARTICLE BEAM APPARATUS

(75) Inventors: Tasuku Yano, Kokubunji (JP); Zhaohui Cheng, Tokyo (JP); Takashi Furukawa, Sagamihara (JP); Osamu Nasu, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 210 days.

(21) Appl. No.: 12/149,218

(22) Filed: Apr. 29, 2008

(65) Prior Publication Data

US 2008/0277583 A1 Nov. 13, 2008

(30) Foreign Application Priority Data

May 9, 2007 (JP) .............................. 2007-124849

(51) Int. Cl.
*G21K 7/00* (2006.01)
*G21G 5/00* (2006.01)
*G01N 23/00* (2006.01)
*H01J 3/14* (2006.01)

(52) U.S. Cl. ...................... 250/311; 250/309; 250/310; 250/399; 250/492.3

(58) Field of Classification Search ................ 250/306, 250/307, 309–311, 396 R, 397, 399, 492.1, 250/492.2, 492.21, 492.3
See application file for complete search history.

(56) References Cited

U.S. PATENT DOCUMENTS 4,763,004 A * 8/1988 Yasuda et al. ............ 250/396 R
6,027,841 A * 2/2000 Suzuki ........................ 430/30
6,992,290 B2 * 1/2006 Watanabe et al. ............ 250/310
2005/0099628 A1 * 5/2005 Kokumai .................... 356/401
2006/0151698 A1 7/2006 Sasaki et al.
2006/0231773 A1 10/2006 Katagiri et al.
2008/0277583 A1 * 11/2008 Yano et al. .................. 250/310
2009/0057557 A1 * 3/2009 Cheng et al. ................ 250/310

FOREIGN PATENT DOCUMENTS

| JP | 06-295695 | 4/1993 |
| JP | 2005-345272 | 6/2004 |
| JP | 2006-173055 | 12/2004 |
| JP | 2006-294481 | 4/2005 |
| JP | 2006-234789 | 10/2005 |
| JP | 2007-285966 | 4/2006 |

* cited by examiner

*Primary Examiner*—Bernard E Souw
(74) *Attorney, Agent, or Firm*—Stites & Harbison PLLC; Juan Carlos A. Marquez, Esq.

(57) ABSTRACT

Electrification affected on a surface of a sample which is caused by irradiation of a primary charged particle beam is prevented when plural frames are integrated to obtain an image of a predetermined area of the sample in a charged particle beam apparatus. The predetermined area of the sample is scanned with a primary electron beam from an electron gun, and plural frames are generated and integrated while detecting generated secondary electrons with a detector to obtain the image of the predetermined area. If it is determined by a detection signal of the detector that an electrification amount at the predetermined area becomes a specified value when generating plural frames, an electricity removal voltage is applied to a boosting electrode to remove or reduce the electrification, prior to generation of the next frame. Accordingly, the signal-to-noise ratio of the image obtained by integrating plural frames can be improved.

17 Claims, 16 Drawing Sheets

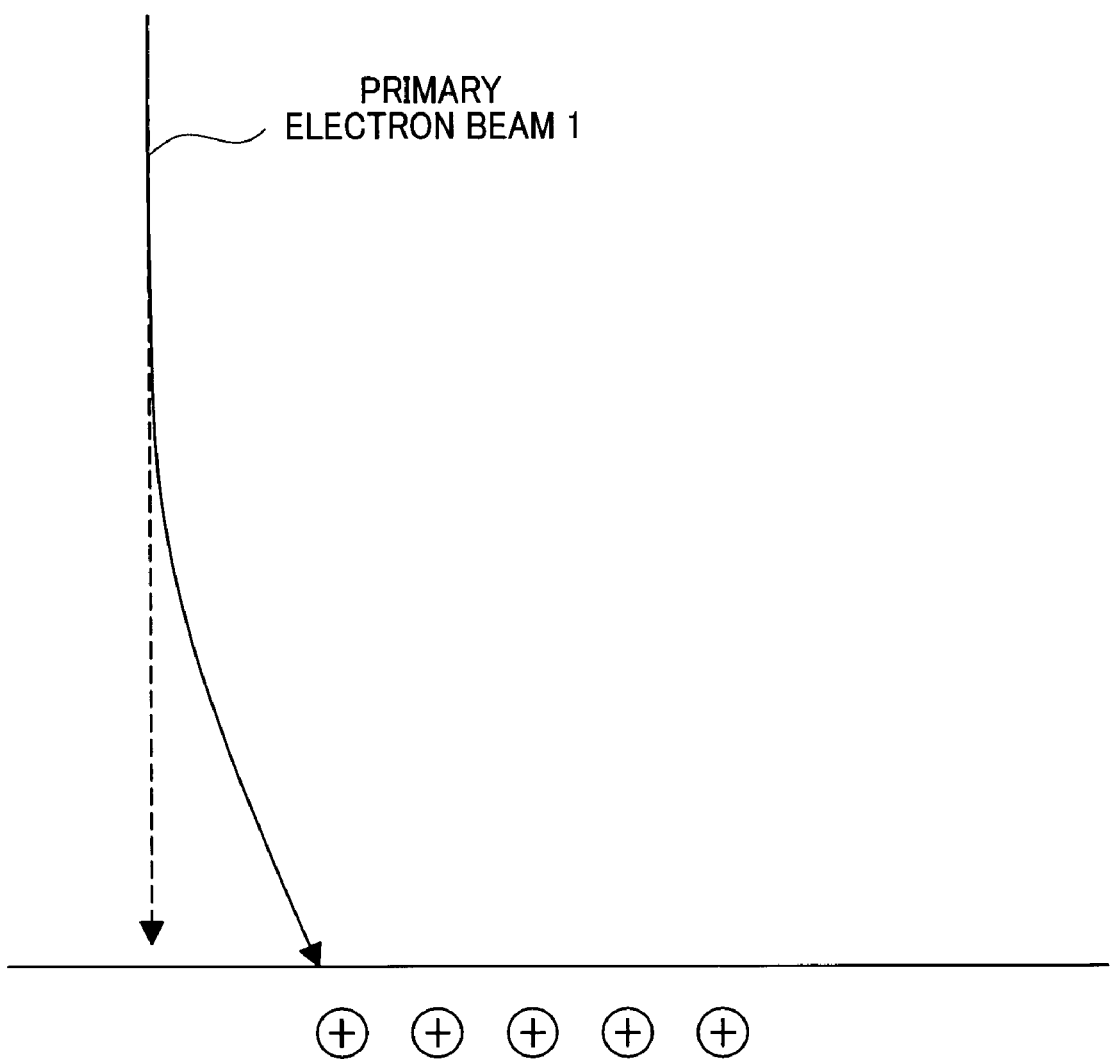

BEING FOCUSED

BEING DEFOCUSED

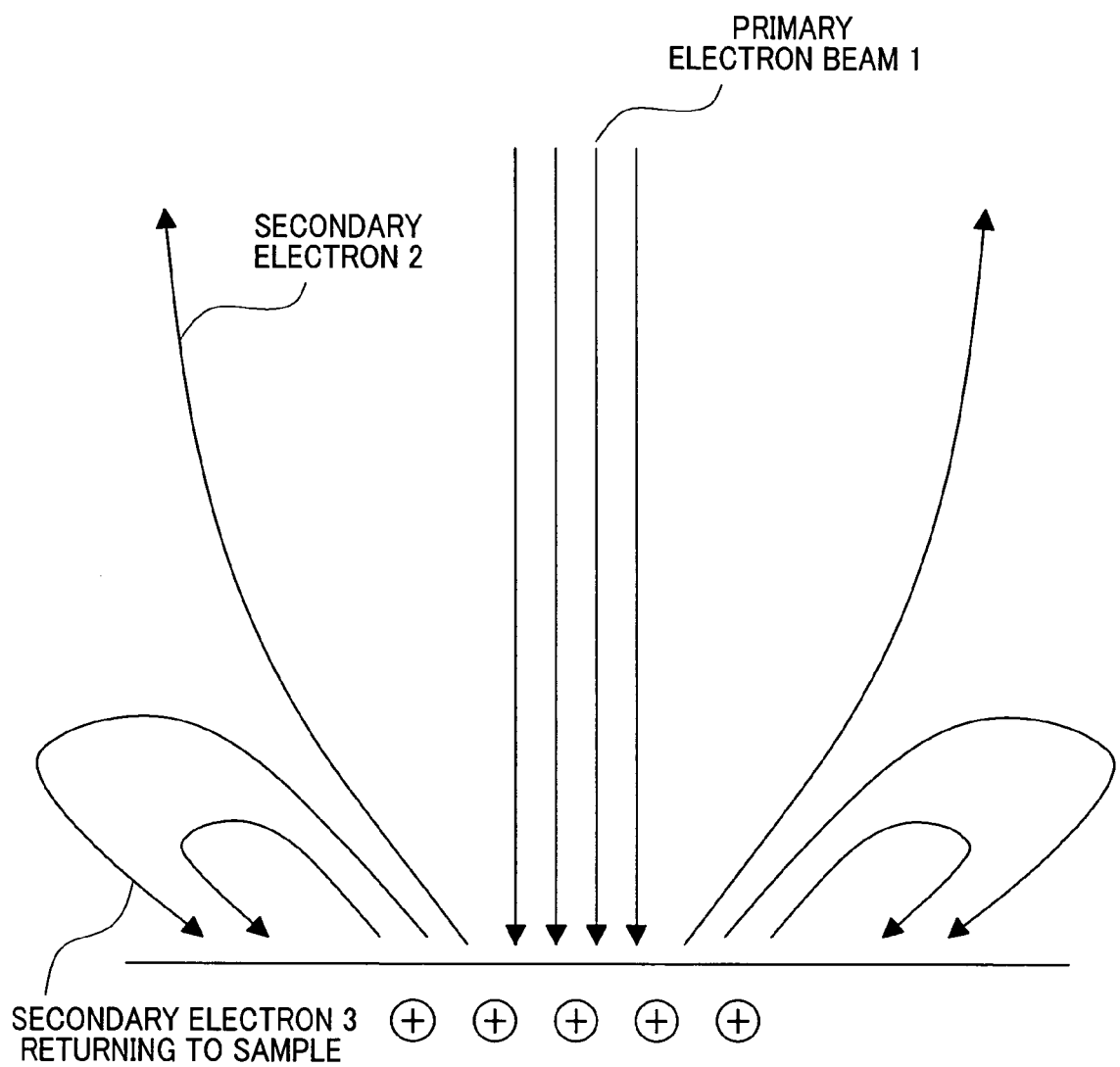

ELECTRIC POTENTIAL ON WAFER

DISTANCE FROM WAFER (μm)

ORBIT OF SECONDARY ELECTRON

ELECTRIC POTENTIAL ON WAFER

DISTANCE FROM WAFER (μm)

ORBIT OF SECONDARY ELECTRON

CHARGED PARTICLE BEAM APPARATUS

CLAIM OF PRIORITY

The present application claims priority from Japanese application JP2007-124849 filed on May 9, 2007, the content of which hereby incorporated by reference into this application.

BACKGROUND OF THE INVENTION

The present invention relates to a charged particle beam apparatus, and particularly to an electrification prevention technique for a wafer in an apparatus for inspecting and measuring the size and shape of a pattern formed on a sample.

Inspection and measurement of the conditions of a circuit pattern formed on a semiconductor wafer during a process of manufacturing a semiconductor device is a technique that plays an important role in improving a yield and establishing reliability. The inspection and measurement is realized by an apparatus using lights or an apparatus using charged particle beams. Particularly, along with miniaturization of a recent semiconductor device, inspection and review using charged particle beams represented by electron beams in a critical dimension scanning electron microscope (CD-SEM) becomes important. However, since a surface of the semiconductor wafer during the manufacturing process is configured by an insulating film made of silicon oxide, silicon nitride, an organic material, a high-dielectric material or the like, when the charged particle beam is irradiated onto the surface of the wafer, the surface of the wafer is electrically charged, and accordingly the orbits of signal particles generated from the surface are changed, resulting in deterioration of a scanned image to be obtained.

Various causes of the image deterioration are conceivable. One of them is an image distortion caused by electrification on the surface of a sample such as a wafer, as shown in FIG. 1. Specifically, an area whose image is already obtained is positively-charged by emission of secondary electrons, and when a scanned image for another area adjacent the area is to be obtained, the orbits of primary electron beams are affected by positive charges of the adjacent area, and the scanned image to be generated is distorted by the detected secondary electrons, resulting in local magnification variation.

As shown in FIGS. 2A and 2B, due to the electrification of the surface of the sample, a focus electric field of the primary electron beam by an objective lens is affected, so that the primary electron beam is changed from a focus state (FIG. 2A) to a defocus state (FIG. 2B), thus deteriorating the resolution of a scanned image to be obtained.

Further, as shown in FIG. 3, the secondary electrons generated from the sample by the positive electrification of the surface of the wafer are attracted by the positive electrification of the surface of the wafer to return to the wafer. Accordingly, efficiency of detecting the secondary electrons varies, resulting in darkness of an entire scanned image to be obtained or local reduction in brightness.

In order to avoid the affect of the electrification on the sample, for example, Japanese Patent Application Laid-Open No. 2005-345272 proposes electrification reduction by a boosting method. In the boosting method, a voltage (boosting voltage) applied to a booster (boosting) electrode incorporated into an objective lens of an SEM is set in accordance with a pattern shape and a material of a sample to be observed, so as to change the electric field intensity of the surface of the sample.

BRIEF SUMMARY OF THE INVENTION

In the charged particle beam apparatus such as the CD-SEM, it is necessary to scan an area of the sample plural times, such as 4 times, 8 times, 16 times, and 32 times to obtain its image, and to integrate plural frames to be obtained in order to improve the signal-to-noise ratio of the image on the basis of a detection amount of the secondary particles to be obtained. This is because it is desirable to decrease the current value of the primary electron beam from the viewpoint of improvement of resolution or prevention of deterioration of a low-resistant sample. On the other hand, this is because it is desirable to irradiate more primary electron beams from the viewpoint of improvement of the signal-to-noise ratio. As a result, when the number of frames to be integrated is increased, the surface of the wafer is electrically charged, and the scanned image to be obtained is largely affected.

However, when plural frames are integrated by scanning the sample to be observed plural times to obtain one image in the conventional boosting method described above, a boosting voltage at the same level that is set in accordance with a pattern shape and a material of the sample to be observed is applied. Therefore, the image to be obtained by integrating plural frames is deteriorated due to the affect of the electrification of the surface of the sample accumulated by irradiation of the electron beam to generate plural frames.

An object of the present invention is to provide a charged particle beam apparatus such as a CD-SEM which obtains an image of a sample by integrating plural frames, and in which the signal-to-noise ratio of the image to be obtained is improved by eliminating the affect of electrification as much as possible.

In order to achieve the above-described object, the present invention provides a charged particle beam apparatus which obtains an image of a predetermined area of a sample by scanning the predetermined area of the sample with a charged particle beam and by detecting a secondary particle generated, and which includes: a charged particle source which generates the charged particle beam; a deflector which scans the predetermined area with the charged particle beam; a detector which detects the secondary particle generated from the sample by scanning the predetermined area with the charged particle beam; an information processing unit to which a detection signal of the detector is input to generate plural frames by scanning the predetermined area with the charged particle beam plural times on the basis of the detection signal and which obtains an image obtained by integrating the plurality of frames generated; and a boosting voltage applying unit which applies an electrification removal voltage between the scans with the charged particle beam to generate the plurality of frames. By employing the configuration of the charged particle beam apparatus, the electrification affected on the respective frames to be integrated can be removed or reduced, and an image with the signal-to-noise ratio improved can be obtained.

Further, in order to achieve the above-described object, the present invention provides a scanning electron microscope including: an electron gun which generates the primary electron beam; a scanning deflector which scans a predetermined area of the sample with the primary electron beam; an objective lens which converges the primary electron beam; a detector which detects a secondary electron generated by irradiation of the primary electron beam to output a detection signal; an information processing unit which obtains an image of the predetermined area by repeating the scanning of the predetermined area with the primary electron beam and by integrating plural frames generated by each scanning on the basis of the detection signal, and determines whether or not it is necessary to remove the electrification on the basis of a signal amount of the frames; a display unit which displays the obtained image; a boosting electrode which applies a boosting voltage to reduce the electrification of the sample between the scans with the primary electron beam for generating the frames on the basis of the determination of the information processing unit; and a boosting voltage control unit which controls the boosting voltage.

In this specification, it should be noted that an image to be obtained is an integrated scanned-image which can be obtained by integrating plural frames, and the frame means scanned image data obtained for each scanning of a sample to be observed. It is obvious that when one image is obtained by integrating plural frames, its field of view (FOV) is not changed.

According to the present invention, it is possible to reduce electrification generated when obtaining an image of a sample to be observed by integrating plural frames and to improve the signal-to-noise ratio of the image.

BRIEF DESCRIPTION OF THE DRAWINGS

FIG. 1 is a diagram for explaining image distortion that is a problem in a conventional charged particle beam apparatus;

FIG. 3 is a diagram for explaining secondary electrons returning to a wafer that is a problem in the conventional charged particle beam apparatus;

DETAILED DESCRIPTION OF THE INVENTION

Figure 2A:
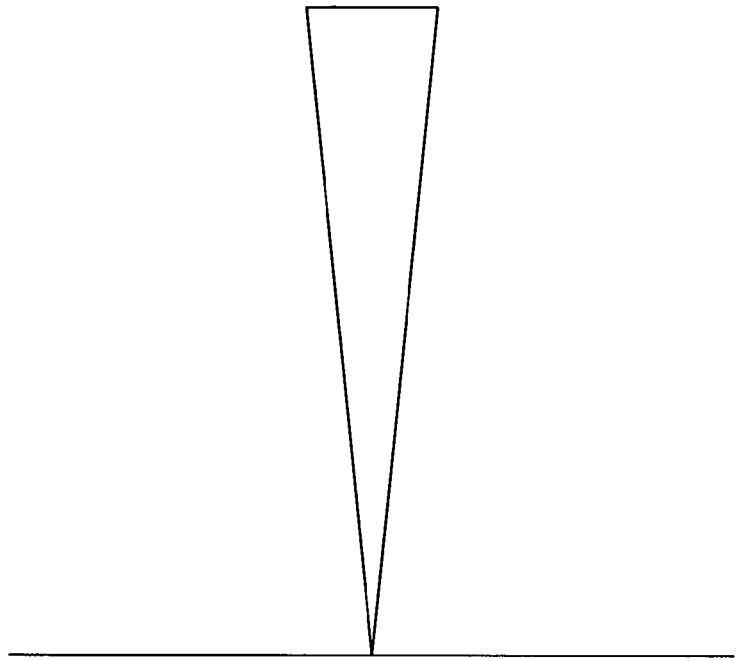
FIG. 2A is a diagram for explaining defocus that is a problem in the conventional charged particle beam apparatus.
Figure 2B:
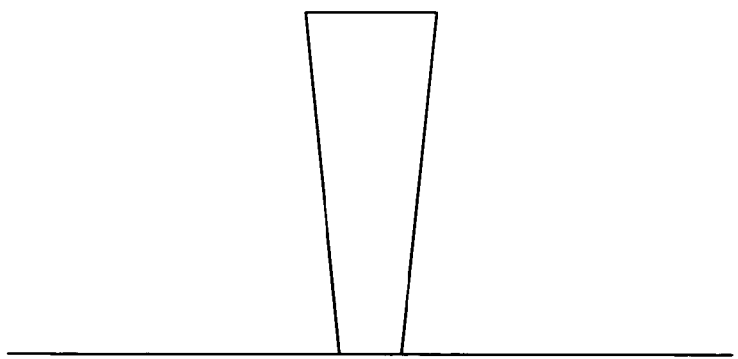
FIG. 2B is a diagram for explaining defocus that is a problem in the conventional charged particle beam apparatus.
Figure 4A:
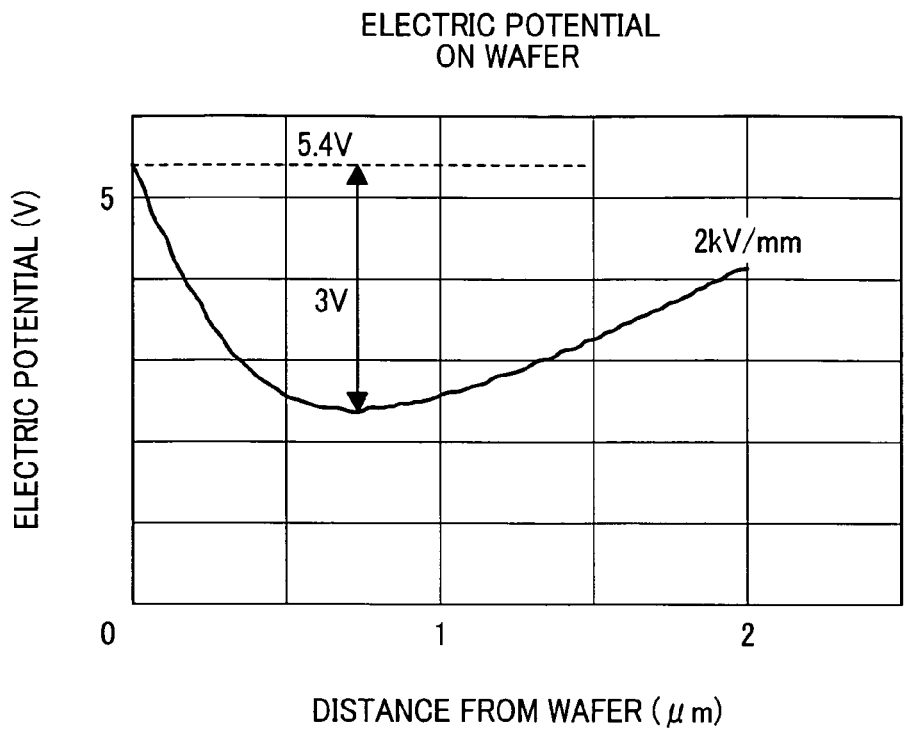
FIG. 4A is a diagram showing a steady state of positive electrification under an intense electric field to explain the principle of the present invention.
Figure 4B:
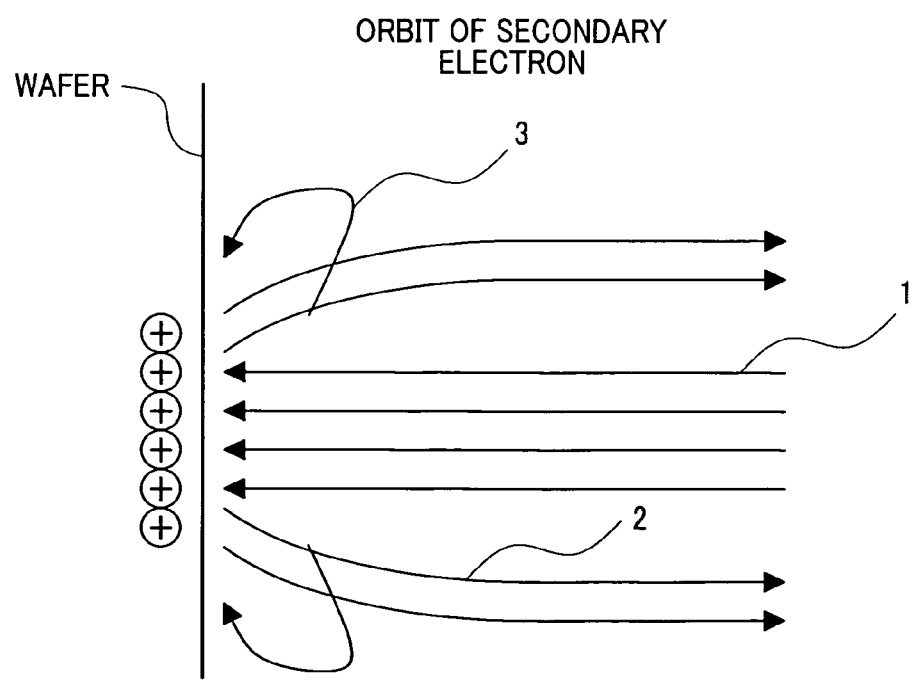
FIG. 4B is a diagram showing a steady state of positive electrification under an intense electric field to explain the principle of the present invention.

Prior to explanation of embodiments of the present invention, the principle of the present invention will be described with reference to FIGS. 4A, 4B, 5A, and 5B. FIGS. 4A and 4B are diagrams each showing an electric potential and orbits of secondary electrons in the vicinity of a surface of a sample (wafer). For example, when frames are overlapped with each other with a field of view (scanning area) of 1 μm under an extracted electric field of 2 kV/mm, the surface of the sample within the field of view is electrically charged up to 5.4V, the failures occur as described in FIGS. 1 to 3. The surface of the sample in this state causes an electric potential barrier of 3V as shown in FIG. 4A. At this time, primary electrons 1 are equal to detected secondary electrons 2, which is in a steady state. Accordingly, if the primary electrons are continuously applied in this state, the failures are not solved.

Figure 5A:
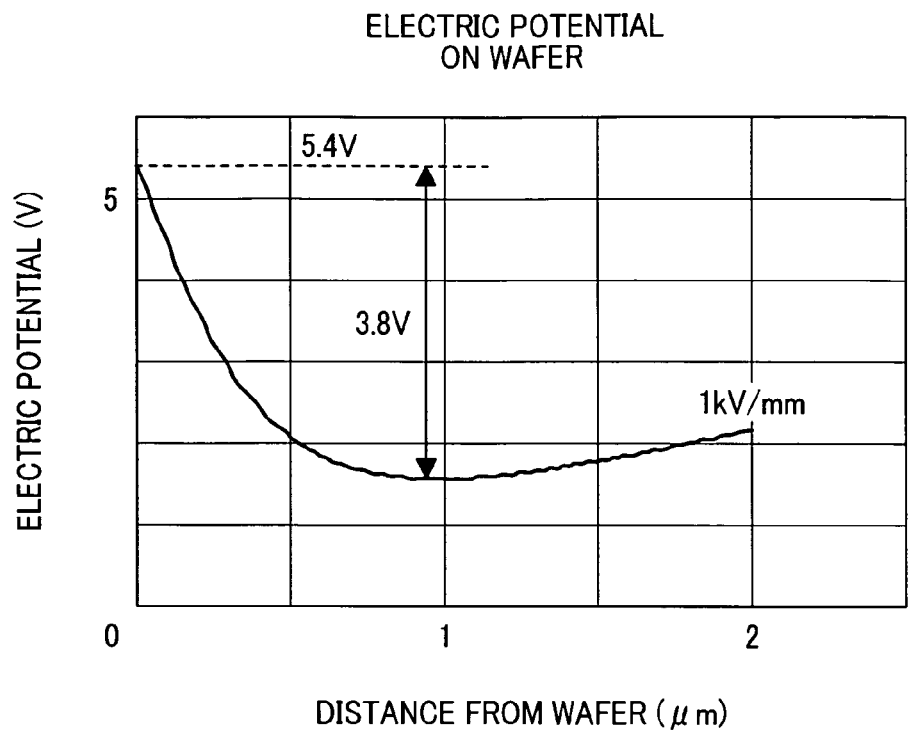
FIG. 5A is a diagram showing a state of reducing positive electrification to explain the principle of the present invention.
Figure 5B:
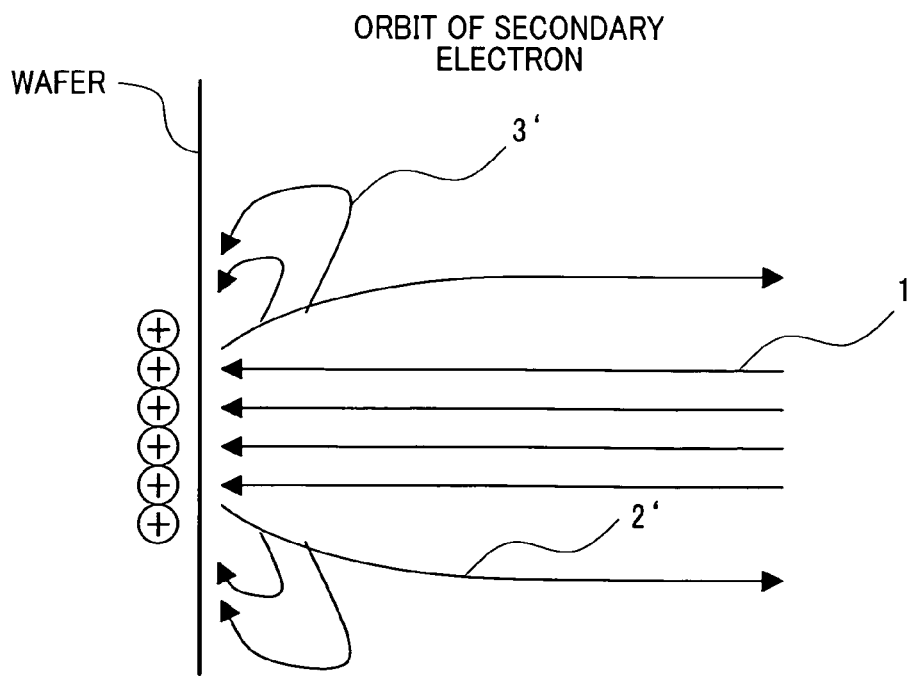
FIG. 5B is a diagram showing a state of reducing positive electrification to explain the principle of the present invention.

On the other hand, the principle of the present invention is to set an electrification removal period during which the electrification is removed between the times the frames are obtained. FIGS. 5A and 5B are diagrams each showing a state in which the extracted electric field is reduced to 1 kV/mm after the surface of the sample becomes the steady state in FIGS. 4A and 4B. Specifically, each of FIGS. 5A and 5B shows a state in which the sample within a field of view (scanning area) of 1 μm is electrically charged up to 5.4V and the extracted electric field is 1 kV/mm. In this state, an electric potential barrier of 3.8 kV is present at a position apart from the sample by about 1 μm as shown in FIG. 5A. When the primary electrons 1 are irradiated, many of the secondary electrons generated return to the sample (wafer) as secondary electrons 2', the returning secondary electrons 2' reduce positive electrification of the wafer. In the present invention, the extracted electric field is preferably controlled by controlling a boosting voltage between the times the frames are obtained, and thus it is possible to obtain a scanned image in which the electrification affected on the wafer is removed or reduced in the following frame acquisition. In addition, it is possible to improve the signal-to-noise ratio of an image obtained by integrating plural frames.

Hereinafter, embodiments of the present invention will be described using the drawings.

First Embodiment

A first embodiment is an embodiment of an SEM which reduces electrification of a wafer by changing a boosting voltage between the times the frames are obtained at the time of sequentially generating plural frames to obtain an image.

Figure 6:
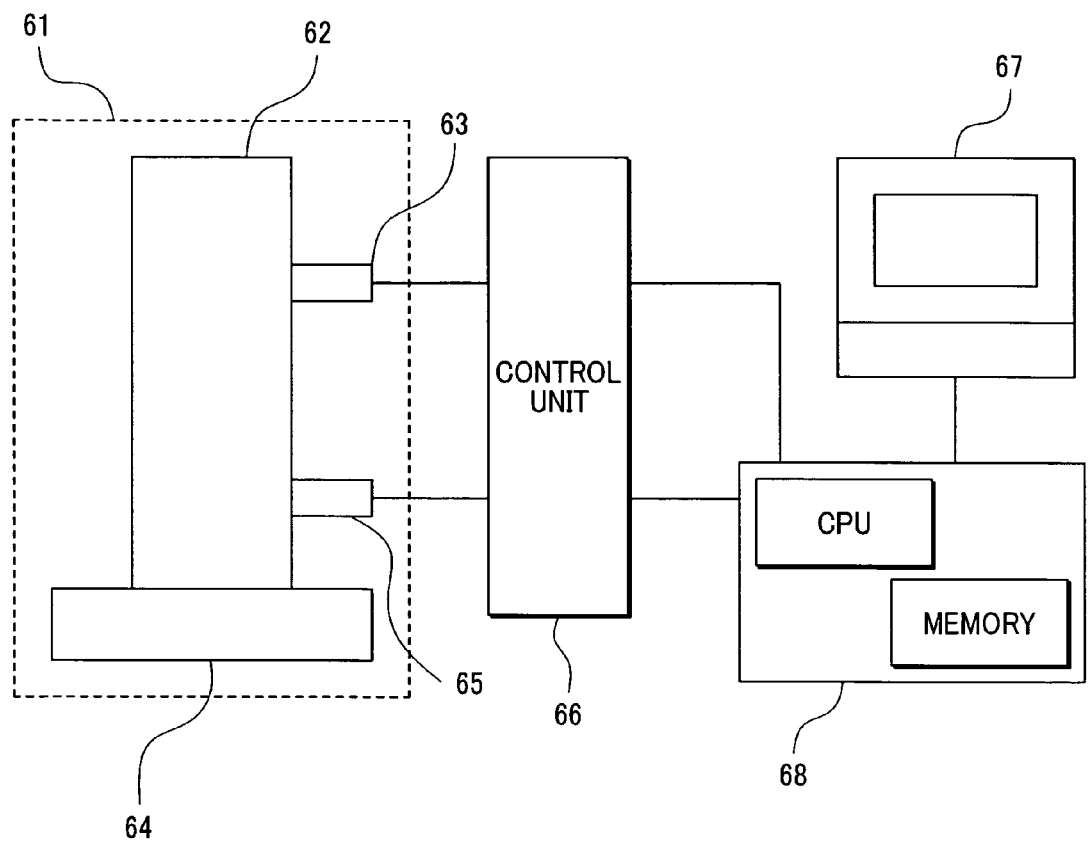
FIG. 6 is a diagram showing an entire configuration of a charged particle beam apparatus (SEM) according to a first embodiment.

FIG. 6 shows an entire configuration of the SEM according to the first embodiment. In FIG. 6, the reference numeral 61 denotes a lens tube and its peripheral equipments of the SEM, 62 denotes the lens tube, 63 denotes a detector for secondary particles such as reflected electrons, 64 denotes a sample chamber in which a sample such as a wafer onto which primary electron beams are irradiated is set, and 65 denotes a boosting power source. The reference numeral 66 denotes a control unit which controls the power source, 67 denotes an image display unit which displays an image obtained by integrating plural frames, and 68 denotes an information processing unit. The information processing unit 68 is configured by an ordinary personal computer (PC) or the like, and includes a CPU as a processing unit, a memory as a memory unit, and an input/output interface unit with the control unit 66 and the image display unit 67. A detection signal of the secondary particles detected by the detector 63 is supplied to the information processing unit 68 through the control unit 66. As will be described later in detail, the information processing unit 68 performs an integrating process for the detection signal received through the control unit 66, and transmits obtained image data of a predetermined area to the image display unit 67. Thus, an image corresponding to the predetermined area of a wafer 78 is displayed on the image display unit 67. Further, as a function of the information processing unit 68, the information processing unit transmits a control signal to the control unit 66. The control unit 66 performs a power source control of the lens tube and its peripheral equipments, the information processing unit 68 computes a control signal necessary for the power source control to be output to the control unit 66.

Figure 7:
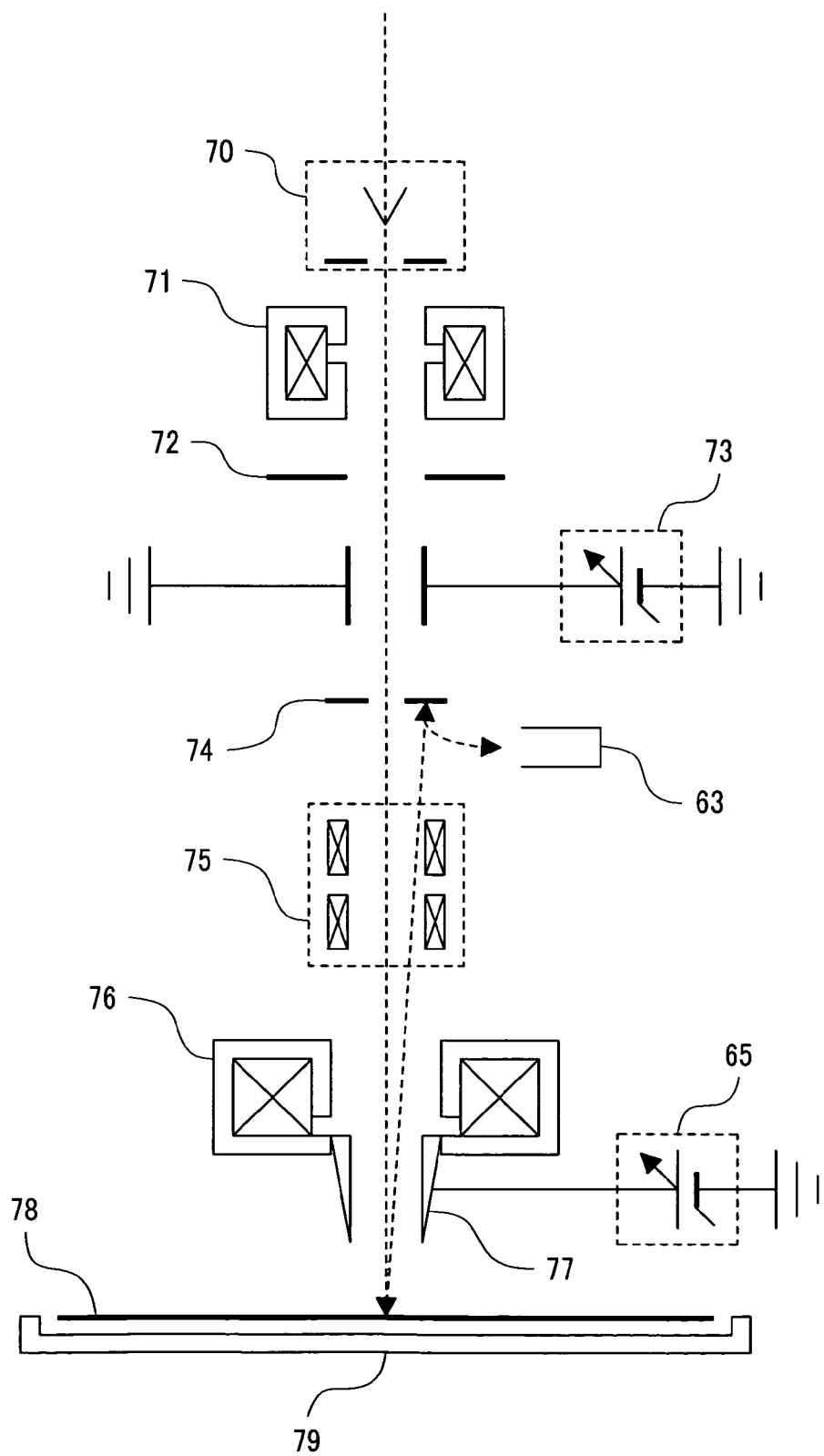
FIG. 7 is a diagram showing a lens tube and its peripheral equipments according to the first embodiment.

FIG. 7 shows an example of a detailed structure of the lens tube and its peripheral equipments of the SEM, denoted by the reference numeral 61, according to the first embodiment. In FIG. 7, the same reference numerals as those in FIG. 6 denote the same constituent elements, 70 denotes an electron gun, 71 denotes a condenser lens which condenses the primary electron beams from the electron gun 70, 72 denotes an aperture, 73 denotes a blanking power source, 74 denotes a reflection plate, 75 denotes a deflector as a deflection scanning unit, 76 denotes an objective lens, 77 denotes a boosting electrode, 78 denotes a wafer, and 79 denotes a stage. The boosting power source 65 applied to the boosting electrode 77 is controlled by the control signal from the control unit 66 as described above. In this specification, it should be noted that the boosting power source 65, functions of the control unit 66 relating to control of the boosting power source 65, and the boosting electrode 77 are referred to as boosting voltage applying units, and the boosting power source 65 and the functions of the control unit 66 relating to control of the boosting power source 65 are referred to as boosting voltage control units in some cases.

As being well known in the art, a predetermined area on the wafer 78 is scanned by the primary electron beam from the electron gun 70 through the deflector 75. The secondary particles generated from the wafer 78 collide with the reflection plate 74 and are reflected therefrom to be detected by the detector 63. As described above, the detection signal of the detected secondary particles is input to the control unit 66, and is converted into a digital signal by an analog/digital converter (A/D converter) (not shown). Then, the digital signal is transmitted to the information processing unit 68, which performs a process such as an integrating process, and an obtained image is displayed on the image display unit 67.

Figure 8:
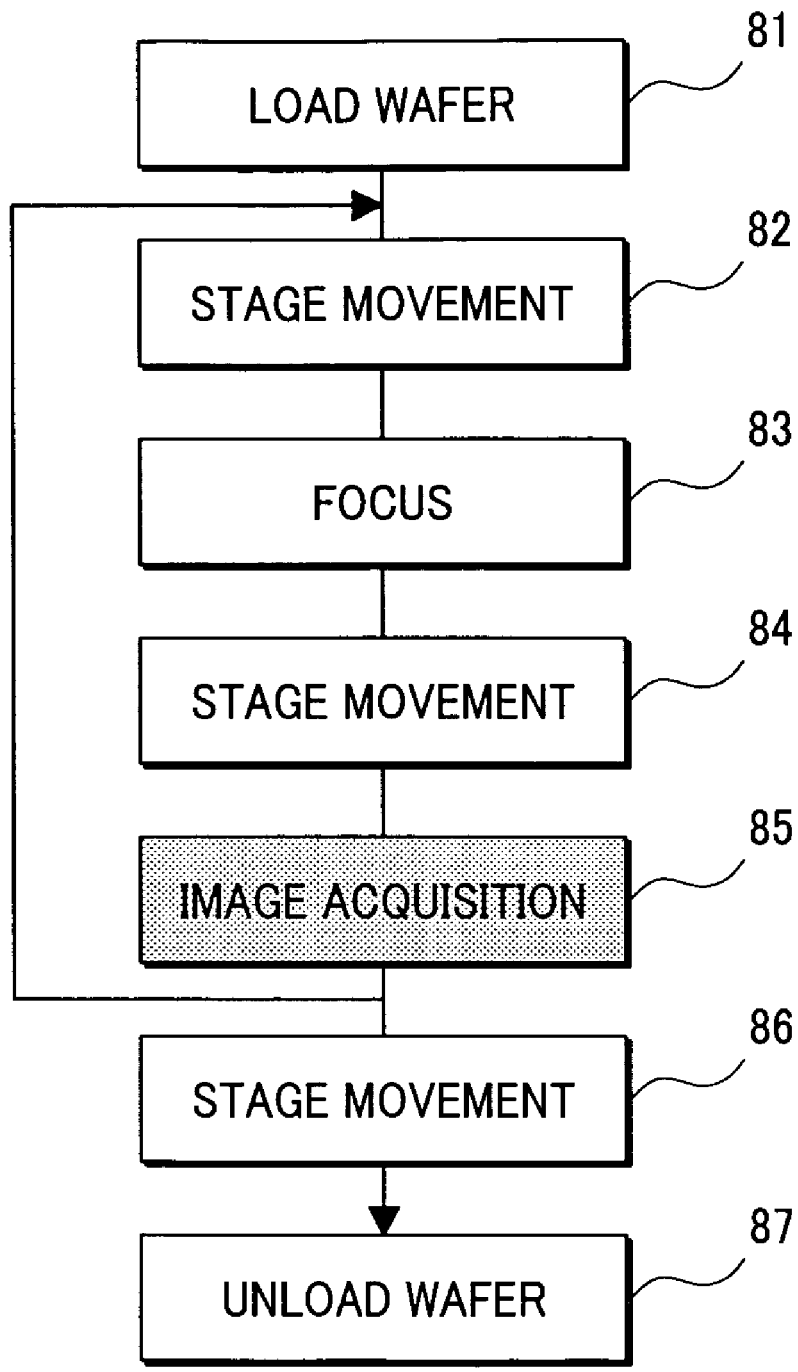
FIG. 8 is a diagram showing a rough flowchart of an operation of the SEM according to the first embodiment.

FIG. 8 is a diagram showing a rough flowchart of an operation in which an image of a predetermined area of a wafer is obtained and a length measurement of the wafer is performed in the SEM of the first embodiment. The flowchart is executed as a program in the CPU of the information processing unit 68 described above. In FIG. 8, the wafer is loaded on the stage 79 (Step 81), and the wafer 78 is set at a focus adjustment position, which is apart from the predetermined area where the primary electron beam is irradiated to obtain an image by 1 to 10 μm, by a first stage movement (Step 82). Then, the primary electron beam is focused on the wafer (Step 83), and the predetermined area of the wafer 78 is set as an image acquisition area by a second stage movement (Step 84). As will be described later in detail, the secondary particles such as the secondary electrons generated from the wafer 78 due to irradiation of the primary electron beam are detected by the detector 63 so as to obtain an image (Step 85). Due to its incomplete flat surface of the wafer, the primary electron beam is focused every time the image of the predetermined area is obtained. In addition, in order to prevent the wafer from being electrically charged when the primary electron beam is focused, the focus adjustment position is different from the predetermined area of the image to be obtained.

Further, an image of a different area such as an area adjacent to the predetermined area on the wafer can be obtained by returning to the stage movement step 82 if needed, and when all images are obtained, the stage is moved (Step 86), and the wafer is unloaded (Step 87).

Figure 9:
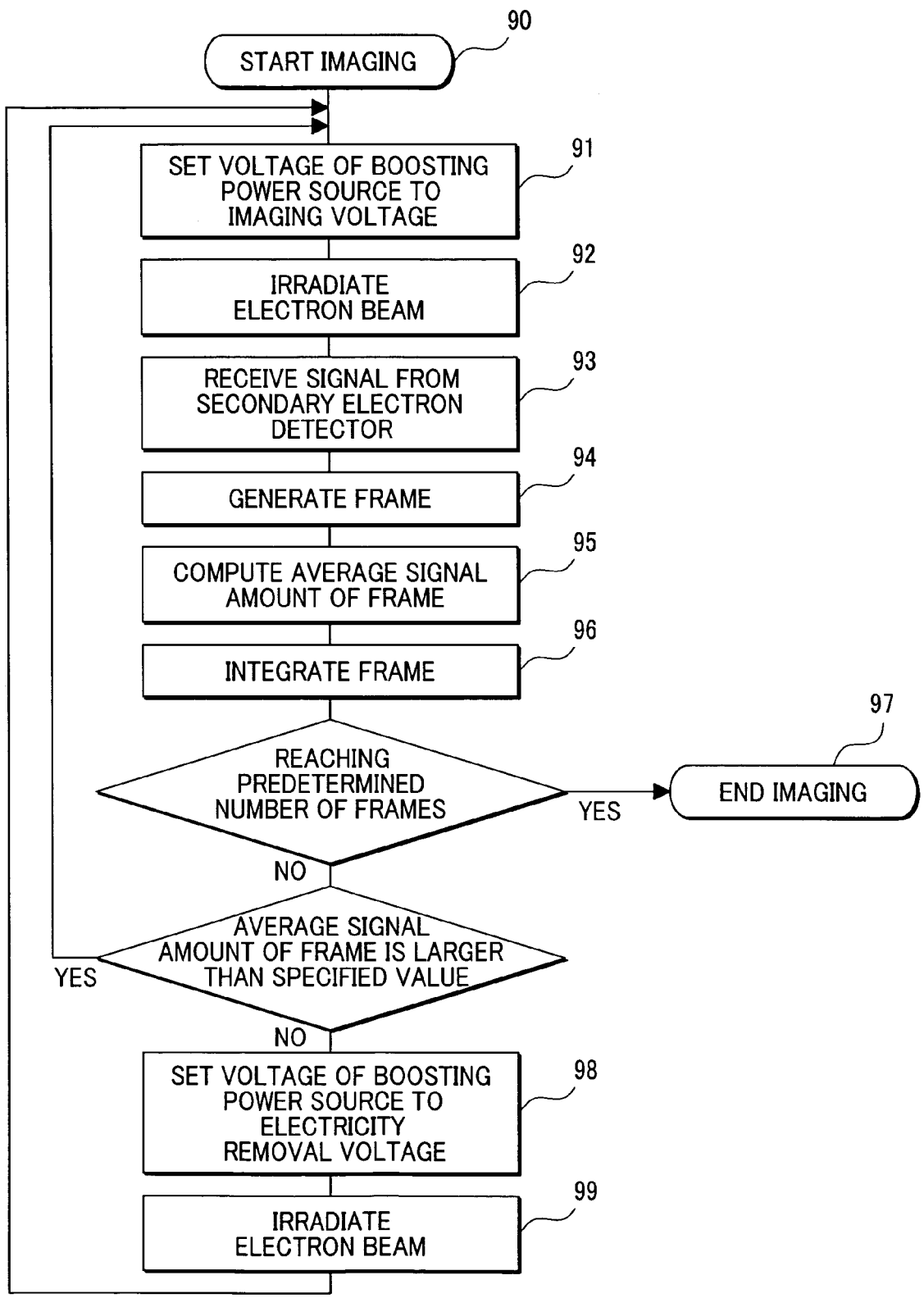
FIG. 9 is a diagram showing a detailed flowchart of image acquisition steps of the operation of the SEM according to the first embodiment.

FIG. 9 is a diagram showing a detailed flowchart of the image acquisition (Step 85) in the flowchart of FIG. 8. The flowchart of FIG. 9 is also realized by a program executed by the CPU of the information processing unit 68. When imaging is started in Step 90, the control unit 66 sets the voltage of the boosting power source 65 to an imaging voltage on the basis of the control signal output from the information processing unit 68 to the control unit 66 (Step 91). It should be noted that the imaging voltage will be described later in detail using FIG. 10. Then, the electron beam (primary electron beam) is irradiated (Step 92). The detection signal from the detector 63 which detects the secondary particles such as the secondary electrons generated from the sample is received by the information processing unit 68 through the control unit 66 (Step 93). The detection signal, namely, scanned image data are used for generating the frame, to be described next, and are used for determining whether or not the boosting voltage is switched in the embodiment.

By using the detection signal, namely, the scanned image data, the frame is generated (Step 94), and is sequentially stored into the memory of the information processing unit 68. In Step 95, an average signal amount of the frames is computed by the CPU, and is similarly stored into the memory as an average signal amount of the latest frames. Further, in Step 96, the obtained frames are integrated with frame-integrated data which are integrated and stored in the memory up to then. When the number of integrations reaches a predetermined number of frames such as 16 and 32, the imaging is completed (Step 97). If the number of integrations does not reach the predetermined number of frames, it is determined whether or not the average signal amount of the latest frames that was computed before is larger than a specified value (threshold). If it is larger than the specified value, the flow returns to Step 91 to generate a new frame. The specified value of the average signal amount is set on the basis of a secondary electron amount in the steady state that was described in the principle of the invention using FIGS. 4A, 4B, 5A and 5B. In the embodiment, if the average signal amount is smaller than the specified value, it is determined that an electricity removal sequence for removing the electrification of the surface of the sample is necessary. Thus, the information processing unit 68 transmits the control signal to the control unit 66, and controls the voltage of the boosting power source 65 to be set to an electricity removal voltage. The electricity removal voltage will be described later in detail.

Figure 10:
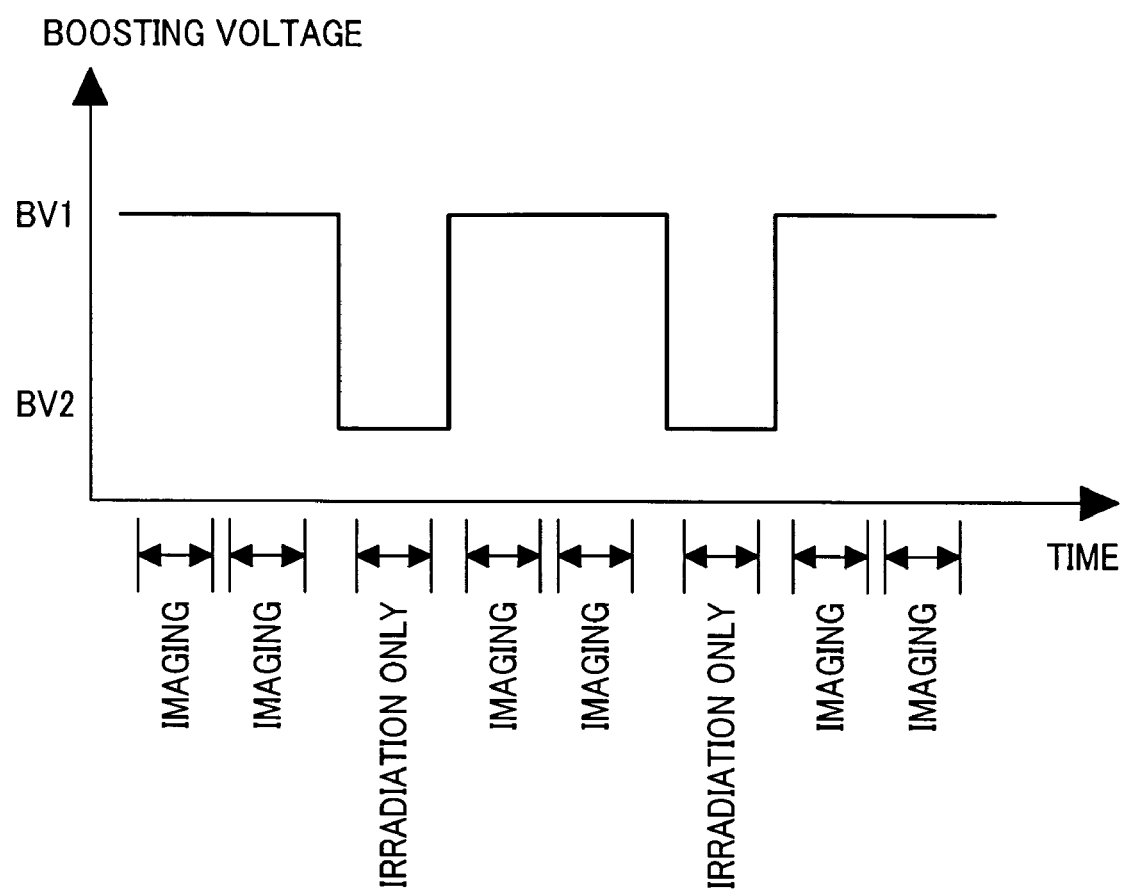
FIG. 10 is a diagram showing a time chart of the operation of the SEM according to the first embodiment.

FIG. 10 schematically shows a time chart of the boosting voltage applied to the boosting electrode 77 by the boosting power source 65 when obtaining an image in the first embodiment. In FIG. 10, "imaging" represents a period of generating one frame. "Irradiation only" represents an electricity removal period and an electrification reduction period during which the electricity removal voltage is applied by the boosting electrode when the primary electron beam is irradiated.

As described above, when an image is obtained, plural frames are imaged in order to integrate a predetermined number of frames. When imaging the frames, a voltage (BV1) at a first level is applied as the boosting voltage. On the other hand, in the electricity removal period and the electrification reduction period during which the primary electron beam is irradiated onto the sample to reduce the electrification, a voltage (BV2) at a second level is applied as the boosting voltage. As being apparent from FIG. 10, the second level (BV2) of the boosting voltage is set lower than the first level (BV1). Accordingly, many of the secondary electrons generated from the sample by irradiation of the primary electron beam return to the sample, and the secondary electron beams that returned to the sample can efficiently remove or reduce the electrification of the sample. The voltage (BV2) at the second level is set to a negative voltage if needed.

According to the first embodiment described above in detail, when plural frames are continuously generated in order to obtain an image by integrating plural frames, the conditions of electrification on the surface of the sample are observed using, for example, the signal amount of the frames. When it is determined that the amount of electrification reaches a predetermined specified-value, the electricity removal sequence for applying the boosting voltage is performed prior to generation of the next frame to reduce the electrification, thus improving the signal-to-noise ratio of the image to be obtained.

Second Embodiment

A second embodiment is an embodiment in which the electrification is reduced by changing the boosting voltage using the electricity removal sequence between the times the frames are obtained, and the effect of electrification reduction is further improved in the electricity removal period and the electrification reduction period by light irradiation and electron beam irradiation.

Figure 11:
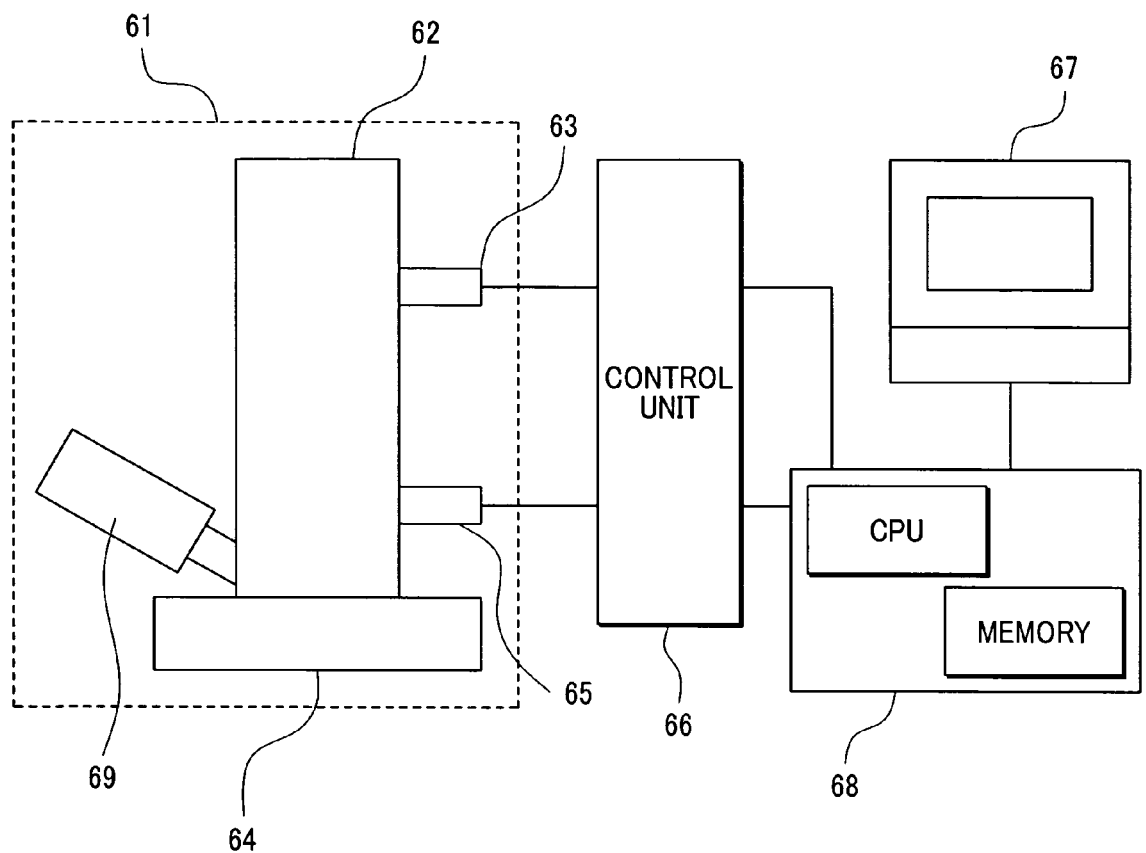
FIG. 11 is a diagram showing an entire configuration of a modified example of an SEM according to a second embodiment.

FIG. 11 shows an entire configuration of an SEM according to the second embodiment. In FIG. 11, the same reference numerals as those in the configuration of the first embodiment shown in FIG. 6 denote the same constituent elements. The reference numeral 69 denotes a second light source (beam irradiation unit for irradiating a light beam or an electron beam) which is additionally provided in the second embodiment and irradiates a light beam such as an electron beam and an ultraviolet light onto the wafer to be observed, so that the reduction of the electrification is further facilitated.

Figure 12:
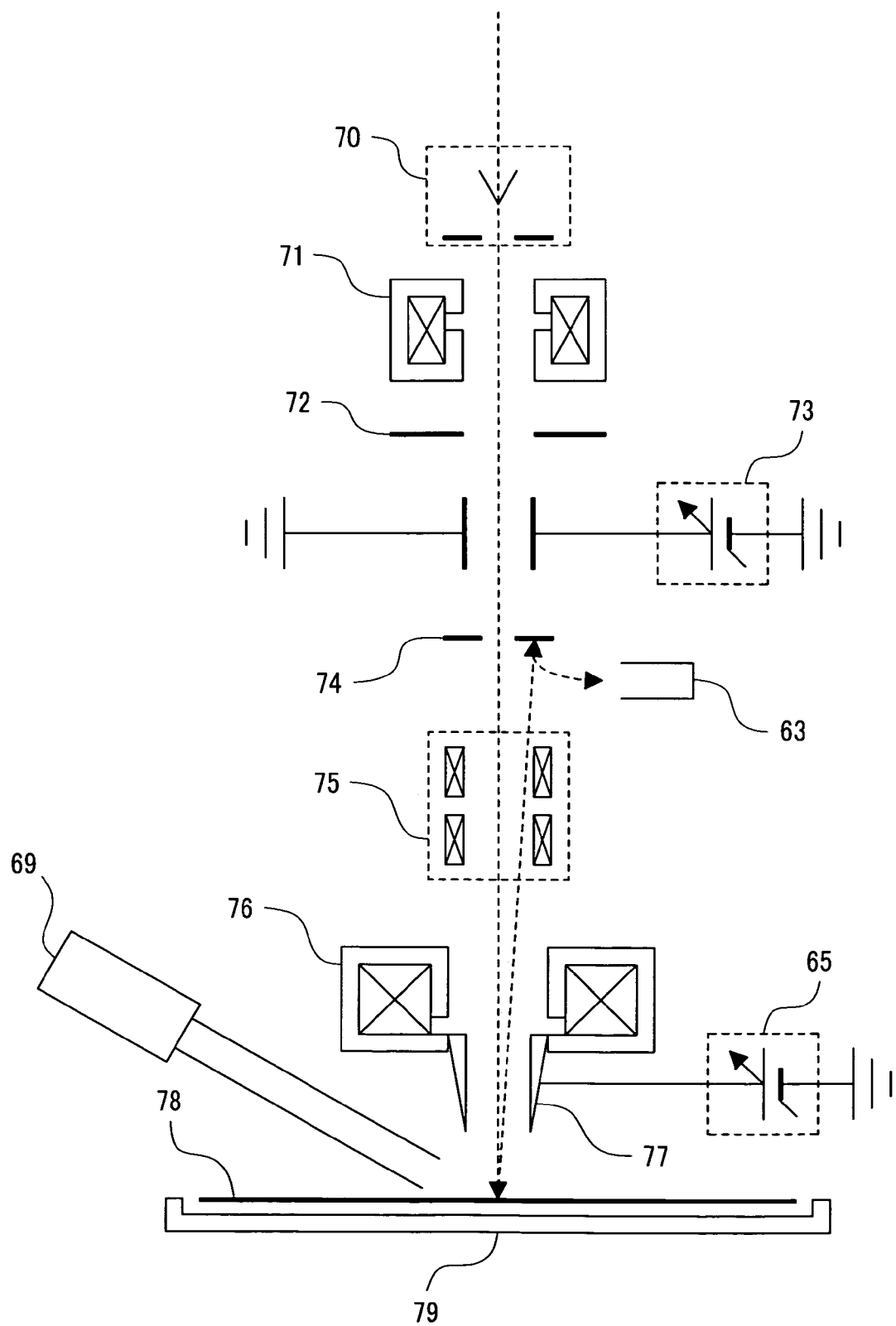
FIG. 12 is a diagram showing a lens tube and its peripheral equipments of the SEM according to the second embodiment.

FIG. 12 shows an example of a detailed structure of the lens tube and its peripheral equipments of the SEM, denoted by the reference numeral 61, according to the second embodiment. In FIG. 12, the same reference numerals as those in FIGS. 7 and 11 denote the same constituent elements. As the second light source 69, for example, an ultraviolet light source is used to be irradiated onto the boosting electrode 77 in the vicinity of the electrically-charged sample to generate optical electrons. Accordingly, the generated optical electrons can efficiently reduce the electrification of the positively-charged wafer to be observed, synergistically with the applying of the boosting voltage in the first embodiment. Although a signal line used for the control signal from the control unit 66 to the second light source 69 is omitted in FIGS. 11 and 12 for the sake of simple explanation, it is obvious that the second light source 69 is controlled to be turned on or turned off by an instruction of the information processing unit 68. In this specification, it should be noted that the constituent elements for reducing the electrification, such as the boosting power source 65, the boosting electrode 77, and the second light source 69, are collectively referred to as electrification reduction control units in some cases.

The operation and the time chart of the SEM according to the second embodiment are the same as those described using FIGS. 8 to 10 in the first embodiment, and timing when the beam is irradiated onto the vicinity of the sample by the second light source 69 corresponds to the periods of "irradiation only" illustrated in the time chart of FIG. 10.

Since an image is obtained by integrating plural frames even in the second embodiment, when plural frames are continuously generated, the conditions of electrification on the surface of the sample are observed. If an electrification amount becomes equal to or less than the predetermined specified-value (threshold), the electricity removal sequence is performed by applying the boosting voltage and by irradiating the electron beam and the light beam prior to generation of the next frame, thus efficiently reducing the electrification.

Third Embodiment

As similar to the first embodiment, a third embodiment is an embodiment of an SEM in which if it is determined that the electricity removal sequence is necessary, the electrification is reduced by applying the electricity removal voltage as the boosting voltage in the electricity removal period and the electrification reduction period to be executed, and the amount of the primary electron beam irradiated onto the sample is controlled, thus effectively reducing the electrification.

Figure 13:
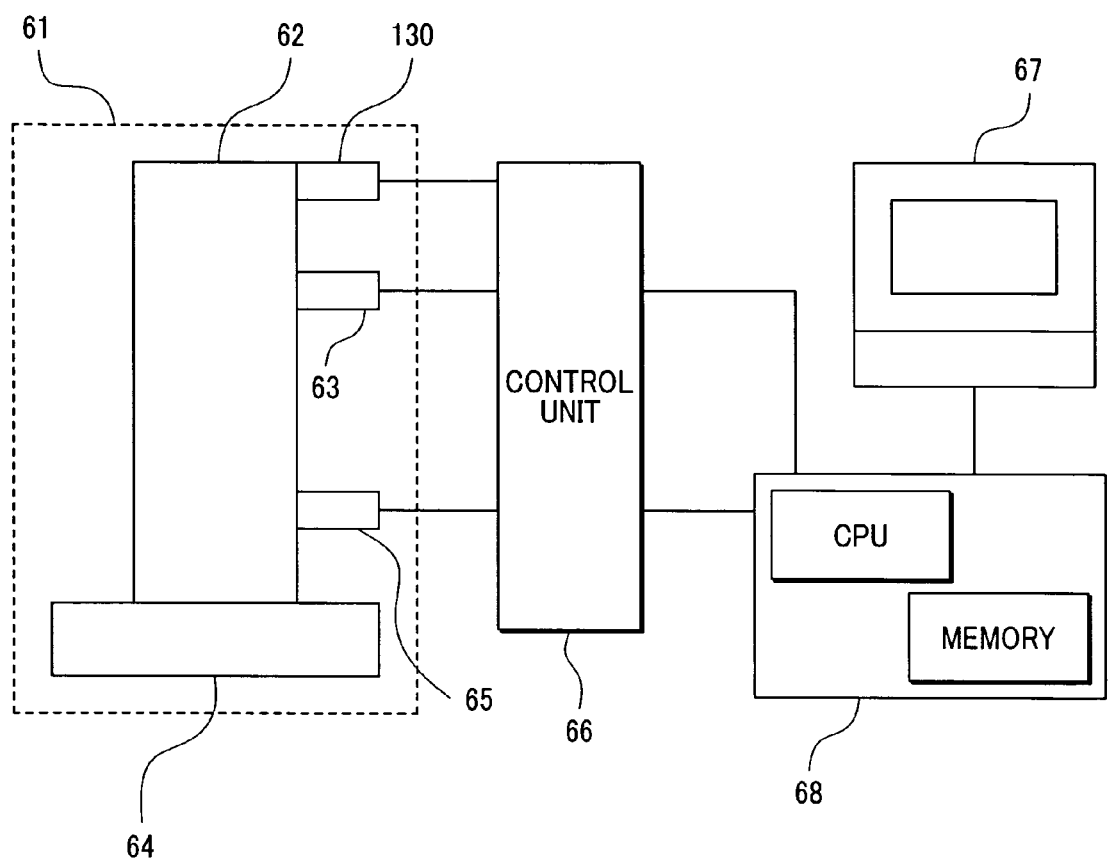
FIG. 13 is a diagram showing an entire configuration of an SEM according to a third embodiment.

FIG. 13 shows an entire configuration of the SEM according to the third embodiment. In FIG. 13, the same reference numerals as those in the first embodiment shown in FIG. 6 denote the same constituent elements. The reference numeral 130 denotes an electrification-reduction electrostatic lens power source which is additionally provided in the third embodiment to function as an electrification-reduction control unit and facilitates reduction of the electrification by controlling the amount of the primary electron beam irradiated onto the sample to be observed.

Figure 14:
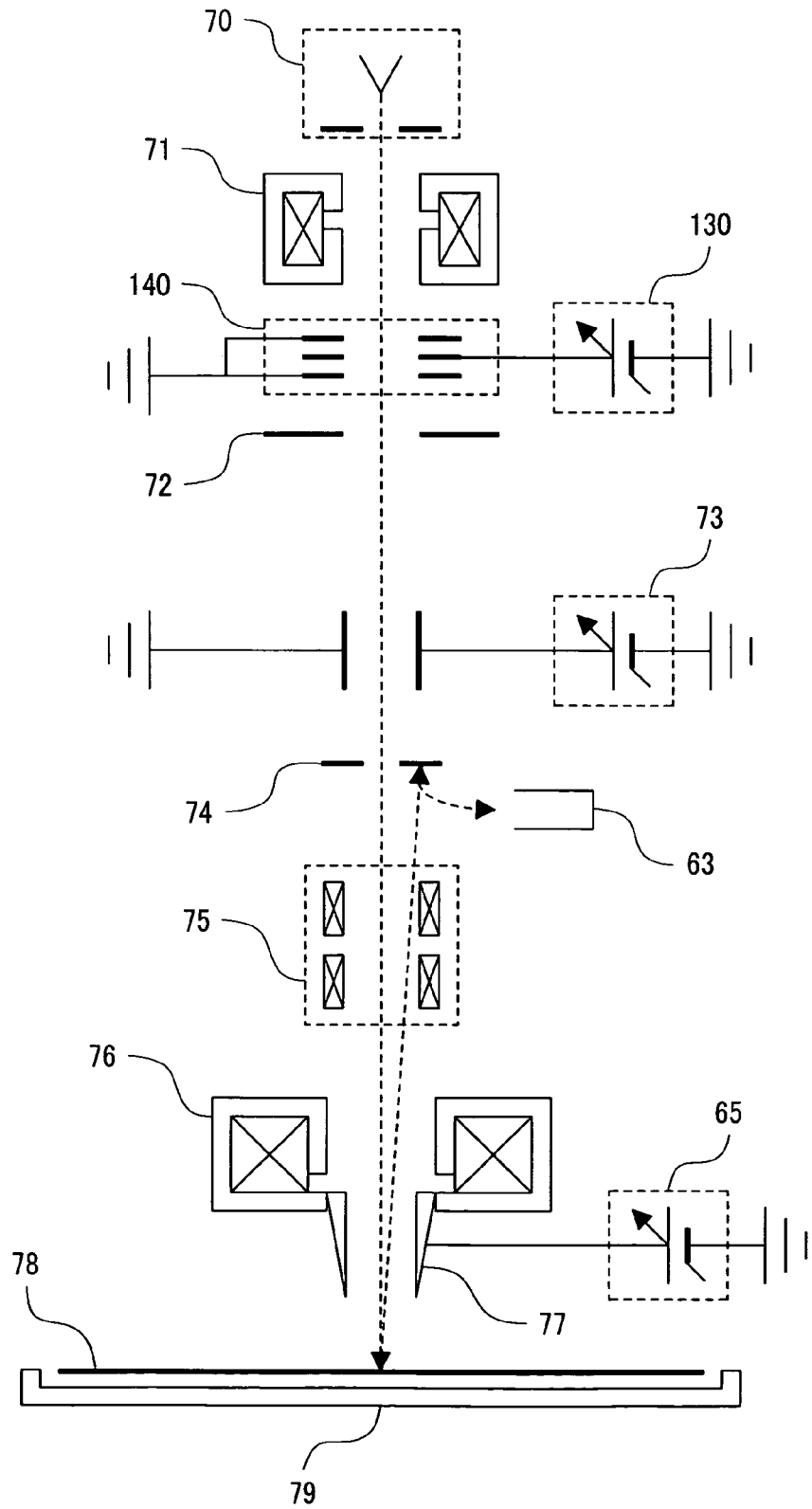
FIG. 14 is a diagram showing a lens tube and its peripheral equipments of the SEM according to the third embodiment.

FIG. 14 shows an example of the lens tube and its peripheral equipments of the SEM, denoted by the reference numeral 61, according to the third embodiment. In FIG. 14, the same reference numerals as those in FIGS. 7 and 13 denote the same constituent elements. The reference numeral 140 denotes an electrostatic lens whose voltage is controlled by the electrostatic lens power source 130 and which can efficiently reduce the electrification of the positively-charged sample by controlling the amount of the primary electron beam from the electron gun 70.

Figure 15:
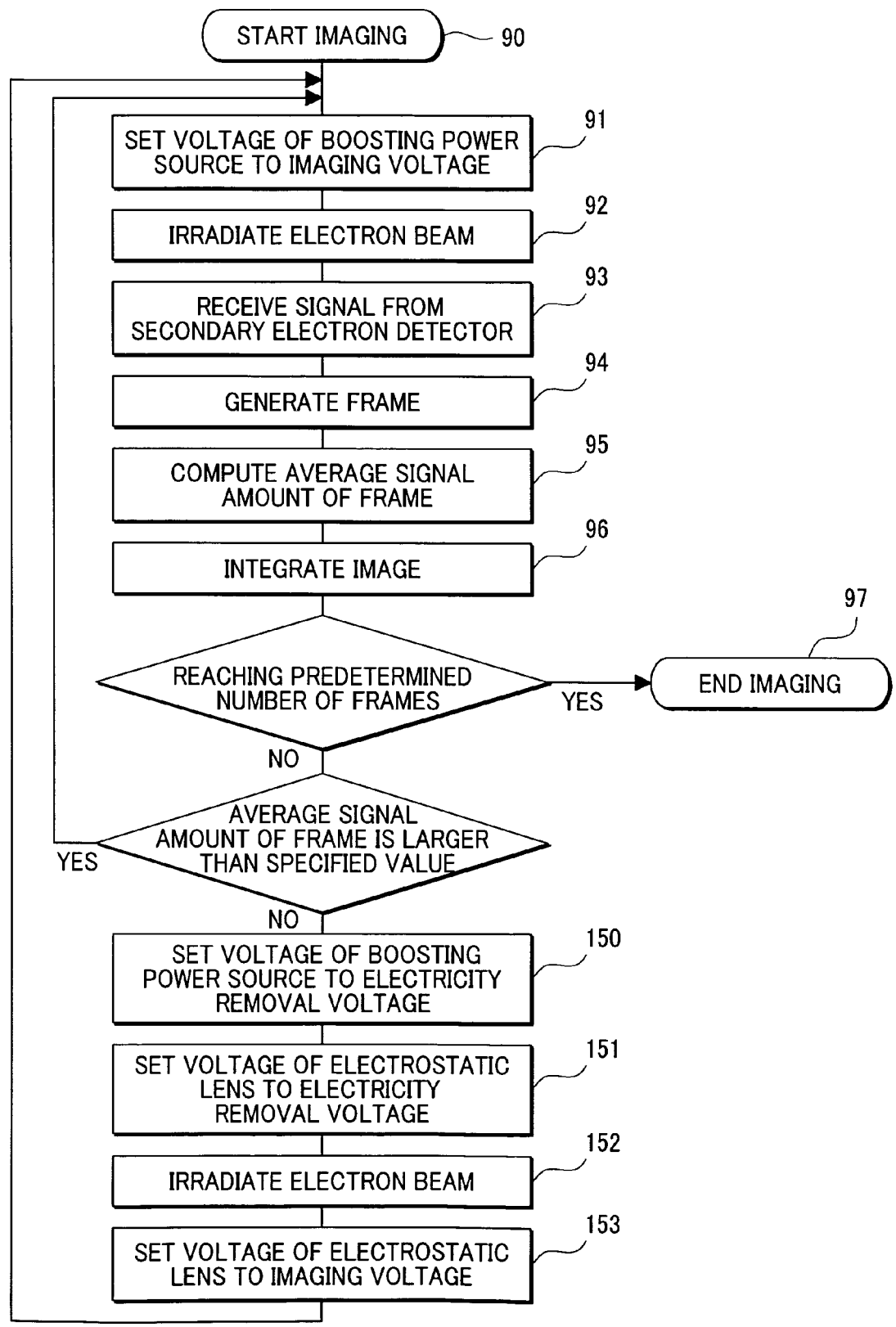
FIG. 15 is a diagram showing a detailed flowchart of image acquisition steps of an operation of the SEM according to the third embodiment.

Since a rough flowchart of an operation of the SEM according to the third embodiment is the same as that described using FIG. 8 in the first embodiment, the explanation thereof will be omitted. FIG. 15 shows a detailed flowchart when an image is obtained in the operation of the SEM according to the third embodiment. In FIG. 15, an imaging starting step 90 to an imaging ending step 97 are the same as those in FIG. 9. In Step 94, when the number of integrated images does not reach a predetermined number of frames and the signal of the frames is less than a specified value, the boosting power source 65 is set to the electricity removal voltage (Step 150), as similar to the first and second embodiments, and a voltage which is generated by the electrostatic lens power source 130 and is applied to the electrostatic lens 140 is set to the electricity removal voltage (Step 151). Then, the electron beam is irradiated onto the sample to reduce the electrification (Step 152). After the electricity removal period and the electrification reduction period during which a high current is irradiated, the voltage of the electrostatic lens 140 is set to the imaging voltage (Step 153), and the flow returns to Step 91 to start the imaging.

Figure 16A:
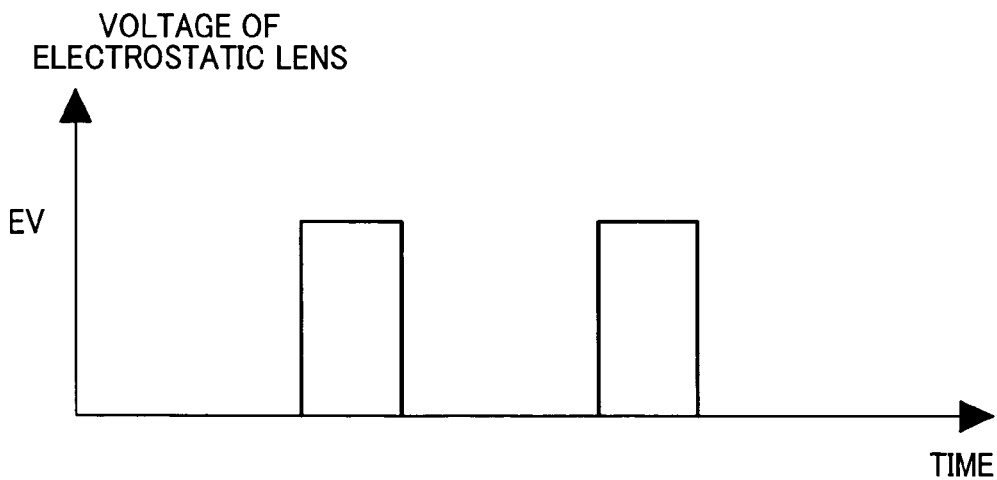
FIG. 16A is a diagram showing a time chart of the operation of the SEM according to the third embodiment.
Figure 16B:
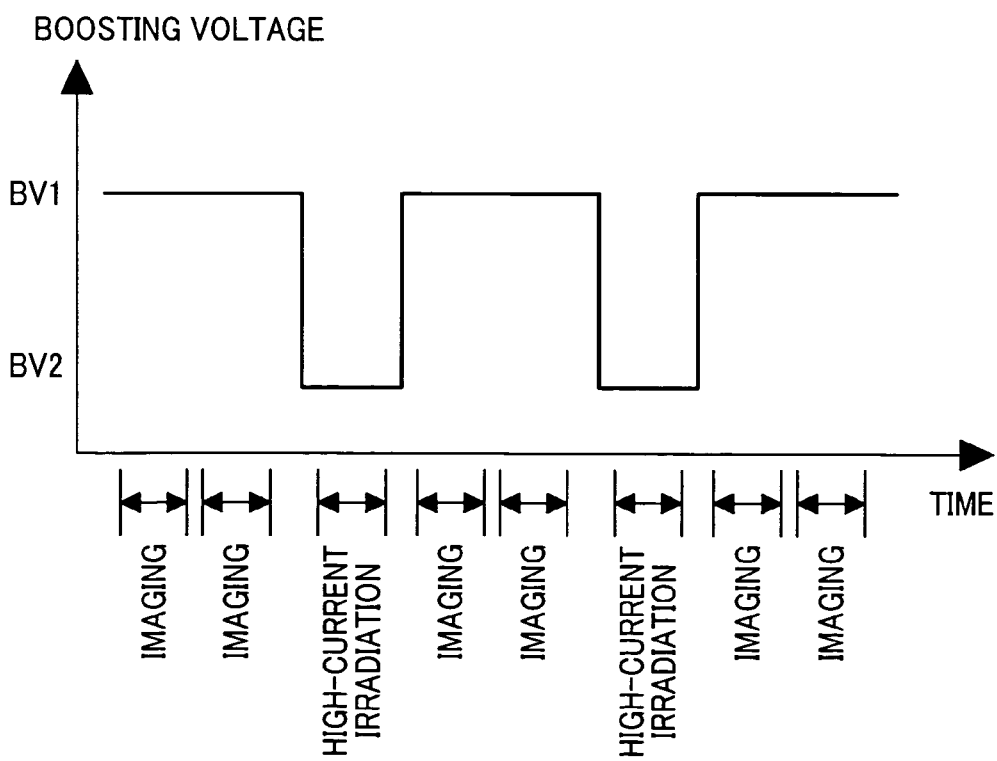
FIG. 16B is a diagram showing a time chart of the operation of the SEM according to the third embodiment.

Next, the electricity removal voltage and the imaging voltage applied to the electrostatic lens 140 in the third embodiment will be described using FIGS. 16A and 16B. In FIG. 16A, shown is an example of a time chart of a voltage applied to the electrostatic lens 140. In FIG. 16B, shown is a time chart of the boosting voltage which is simultaneously applied to the boosting electrode 77. As being apparent from FIGS. 16A and 16B, since a predetermined number of frames are integrated when an image is obtained even in the third embodiment, the frames are continuously imaged. The voltage applied to the electrostatic lens 140 when the frames are imaged is set to 0. Further, as being apparent from FIG. 16B, the boosting voltage is set to the voltage (BV1) at the first level.

On the other hand, in the electricity removal period and the electrification reduction period (the periods illustrated as "high-current irradiation" in FIG. 16) during which a high-current electron beam is irradiated onto the sample between the times the frames are obtained to reduce the electrification in the third embodiment, a predetermined voltage (EV) is applied to the electrostatic lens 140. As the boosting voltage simultaneously applied to the boosting electrode 77, the voltage (BV2) at the second level is applied. As being apparent from FIG. 16A, a predetermined positive voltage is applied to the electrostatic lens 140, the primary electron beam from the electron gun 70 is converged at the position of the aperture 74, the amount of the primary electron beam passing through the aperture 74 is increased, and the high-current electron beam is irradiated onto the sample. As similar to the first embodiment, since the second level of the boosting voltage is set lower than the first level thereof in this period, many of the secondary electrons generated from the wafer by irradiation of the primary electron beam return to the wafer, and the secondary electron beams returned to the wafer can efficiently reduce the positive electrification of the sample together with the increase of the secondary electrons emitted by the high-current irradiation.

Although the various embodiments of the present invention have been described in detail, it is obvious that the present invention is not limited to these embodiments. In the above-described embodiments, there has been exemplified and explained a case in which the surface of the sample is positively charged. However, even in the case where the surface of the wafer is negatively charged, the same effects can be obtained by appropriately selecting the boosting voltage between the times the frames are obtained and the voltage applied to the electrostatic lens. Further, in the above-described embodiments, the average signal amount of the frames computed from the detection signal of the secondary electrons is used to detect the conditions of electrification. However, it is obvious that other methods can be used. For example, an electrification reduction time constant of the sample to be observed is preliminarily stored in the memory of the information processing unit 68, and the conditions of electrification are determined on the basis of the electrification reduction time constant. Accordingly, it is possible to determine where to insert the electricity removal period and the electrification reduction period between the frames.

Further, the structure of the electrode to which the boosting voltage is applied may be one other than those of the boosting electrode 77 shown in FIGS. 7, 12, and 14. Furthermore, although the SEM has been exemplified and explained as the charged particle beam apparatus, it is obvious that the present invention can be applied to a charged particle beam apparatus using a charged particle beam such as an ion beam, as the primary charged particle beam, other than the primary electron beam.

As described above in detail, in the charged particle beam apparatus of the present invention for obtaining an image of the sample to be observed by integrating plural frames, it is determined whether or not the electricity removal or the electrification reduction is necessary between the times the frames are obtained in accordance with the amount of the secondary particles detected in the respective frames. Accordingly, it is possible to reduce the electrification generated when the same area is scanned with the primary charged particle beam to obtain plural frames and to improve the signal-to-noise ratio of an image of a predetermined area obtained by integrating plural frames.

What is claimed is:

1. A charged particle beam apparatus which obtains an image of a predetermined area of a sample by scanning the predetermined area of the sample with a charged particle beam and by detecting a secondary particle generated, the apparatus comprising:

a charged particle source which generates the charged particle beam;

a deflector which scans the predetermined area with the charged particle beam;

a detector which detects the secondary particle generated from the sample by scanning the predetermined area with the charged particle beam;

an information processing unit to which a detection signal of the detector is input to generate a plurality of frames by scanning the predetermined area with the charged particle beam plural times on the basis of the detection signal and which obtains an image obtained by integrating the plurality of frames generated; and a boosting voltage applying unit which applies an electrification removal voltage between the scans with the charged particle beam to generate the plurality of frames.

2. The charged particle beam apparatus according to claim 1, further comprising a beam irradiation unit which irradiates a light beam or an electron beam onto the vicinity of the predetermined area, wherein when the electrification removal voltage is applied, the beam irradiation unit irradiates the light beam or the electron beam onto the vicinity of the predetermined area.

3. The charged particle beam apparatus according to claim 1, further comprising a beam current switching unit which switches a beam current of the charged particle beam from the charged particle source, wherein when the electrification removal voltage is applied, the beam current switching unit switches the beam current to a higher current as compared to that at the time of generating the frames.

4. The charged particle beam apparatus according to claim 1, wherein the information processing unit computes an average signal amount of the frames on the basis of the detection signal, and when the average signal amount becomes equal to or less than a predetermined threshold, the information processing unit controls the boosting voltage applying unit to apply the electrification removal voltage.

5. The charged particle beam apparatus according to claim 1,
wherein the information processing unit controls the boosting voltage applying unit to apply the electrification removal voltage on the basis of an electrification reduction time constant of the sample.

6. A charged particle beam apparatus which obtains an image of a predetermined area of a sample by scanning the predetermined area of the sample with a charged particle beam and by detecting a secondary particle generated, the apparatus comprising:
a charged particle source which generates the charged particle beam;
a deflection scanning unit which scans the predetermined area with the charged particle beam;
a detector which detects the secondary particle generated from the sample by scanning the predetermined area with the charged particle beam;
an information processing unit to which a detection signal of the detector is input to obtain the image by integrating a plurality of frames generated by scanning the predetermined area with the charged particle beam on the basis of the detection signal and which detects conditions of electrification at the predetermined area to determine whether or not it is necessary to reduce the electrification; and
an electrification reduction control unit which controls to reduce the electrification between the times the frames are generated on the basis of the determination of the necessity of the electrification reduction by the information processing unit.

7. The charged particle beam apparatus according to claim 6,
wherein the electrification reduction control unit comprises a boosting electrode which applies a boosting voltage and a boosting voltage control unit which controls the boosting voltage.

8. The charged particle beam apparatus according to claim 7,
wherein: the electrification reduction control unit further comprises a beam irradiation unit which irradiates a light beam or an electron beam onto the vicinity of the predetermined area; and
the beam irradiation unit irradiates the light beam or the electron beam onto the vicinity of the predetermined area when the electrification is reduced between the times the frames are generated.

9. The charged particle beam apparatus according to claim 7,
wherein the electrification reduction control unit further comprises a current switching control unit which controls to switch a beam current of the charged particle beam from the charged particle source, and controls the beam current to be a higher current when the electrification is reduced between the times the frames are generated.

10. The charged particle beam apparatus according to claim 6,
wherein the information processing unit detects conditions of the electrification at the predetermined area by computing an average signal amount of the detection signal by which the frames are generated.

11. The charged particle beam apparatus according to claim 10,
wherein the information processing unit controls the electrification reduction control unit to reduce the electrification between the times the frames are generated when the average signal amount becomes equal to or less than a predetermined threshold.

12. The charged particle beam apparatus according to claim 7,
wherein the information processing unit detects conditions of the electrification at the predetermined area by computing the average signal amount of the detection signal by which the frames are generated.

13. The charged particle beam apparatus according to claim 12,
wherein the boosting voltage control unit controls the boosting voltage to be applied to the boosting voltage applying unit to reduce the electrification between the times the frames are generated when the average signal amount becomes equal to or less than the predetermined threshold.

14. A charged particle beam apparatus which obtains a two-dimensional image of a sample by scanning the sample with a primary electron beam, the apparatus comprising:
an electron gun which generates the primary electron beam;
a scanning deflector which scans a predetermined area of the sample with the primary electron beam;
an objective lens which converges the primary electron beam;
a detector which detects a secondary electron generated by irradiation of the primary electron beam to output a detection signal;
an information processing unit which obtains an image of the predetermined area by repeating the scanning of the predetermined area with the primary electron beam and by integrating a plurality of frames generated by each scanning on the basis of the detection signal, and determines whether or not it is necessary to remove the electrification on the basis of a signal amount of the frames;
a display unit which displays the obtained image;
a boosting electrode which applies a boosting voltage; and
a boosting voltage control unit which controls the boosting voltage to remove the electrification of the sample between the scans with the primary electron beam for generating the frames on the basis of the determination of the information processing unit.

15. The charged particle beam apparatus according to claim 14,
wherein the information processing unit controls the boosting voltage control unit to remove the electrification of the sample when the signal amount of the frames becomes equal to or less then a predetermined threshold.

16. The charged particle beam apparatus according to claim 15, further comprising a beam irradiation unit which irradiates a light beam or an electron beam onto the vicinity of the predetermined area,
wherein when the electrification is removed between the times the frames are generated, the beam irradiation unit irradiates the light beam or the electron beam onto the vicinity of the predetermined area.

17. The charged particle beam apparatus according to claim 15, further comprising a beam current control unit which controls a beam current of the charged particle beam from the charged particle source,
wherein when the electrification is removed between the times the frames are generated, the beam current control unit controls the beam current to be a higher current as compared to that at the time of generating the frames.

* * * * *